United States Patent

Diaz

[11] 4,041,937
[45] Aug. 16, 1977

[54] MEDICAL IMPLEMENT

[76] Inventor: Marcellina Diaz, 114-18 209th St., St. Albans, N.Y. 11411

[21] Appl. No.: 716,531

[22] Filed: Aug. 23, 1976

[51] Int. Cl.$^2$ .............................................. A61B 1/24
[52] U.S. Cl. ...................................... 128/15; 128/136
[58] Field of Search ................ 128/15, 136, 359, 360, 128/147, 208, 12, 13, 16, 20

[56] References Cited
U.S. PATENT DOCUMENTS

| 109,874 | 6/1870 | Osborn | 128/15 |
|---|---|---|---|
| 2,857,908 | 10/1958 | Cornfield | 128/15 |
| 2,882,893 | 4/1959 | Godfroy | 128/136 |
| 3,324,849 | 6/1967 | Kravitz | 128/15 |
| 3,971,370 | 7/1976 | Halford et al. | 128/136 |

Primary Examiner—Robert W. Michell
Assistant Examiner—Henry S. Layton
Attorney, Agent, or Firm—Natter & Natter

[57] ABSTRACT

A tongue blade having a pressure pad for firmly depressing and holding a patient's tongue. The blade includes an attachable bite guard for protecting the patient's teeth and for maintaining a clear air passageway through the patient's mouth. A depth guide prevents overinsertion of the blade. In a modified embodiment the pressure pad is premoistened with an antiseptic solution.

10 Claims, 5 Drawing Figures

MEDICAL IMPLEMENT

BACKGROUND OF THE INVENTION

1. Field of the Invention

This invention relates to a medical implement and especially to a first aid device for use during convulsive seizures.

In particular, the device of this invention concerns a medical implement in the form of a tongue blade.

2. Description of the Prior Art

Convulsive disorders such as epilepsy are symptomatically characterized by recurrent seizures. The occurrence of these sudden attacks can also result from nonepileptic phenomena. First aid treatment for such patients currently includes protective measures to prevent choking, broken teeth, biting of the tongue, and for maintaining a clear air passage. If such an attack occurs within the confines of a medical facility, a doctor, nurse or hospital attendant frequently inserts a conventional wood tongue depressor into the patient's mouth for the duration of the spell. A disadvantage of this procedure especially when used by untrained personnel is that the tongue depressor can be improperly inserted and may provoke choking, damage to the mouth and surrounding tissue or blockage of the air passageway resulting in possible suffocation. Furthermore, such conventional tongue depressors are frequently incapable of preventing tongue biting.

A further shortcoming of this known procedure is that it does not provide any positive measures for tooth protection or for maintaining an open passageway through the mouth.

An additional defect is inherent in the fact that tongue depressors generally available are not specifically designed for this purpose and therefore are not provided in sufficient length, nor do they include elements for firmly gripping one end of the instrument.

The medical appliance of the present invention overcomes many of these disadvantages and accordingly includes a tip portion having a cushioned pressure pad with a gripping surface at the other end for facilitating manipulation of the appliance. The instrument further incorporates a mouthpiece having a bite guard and a depth guide to prevent injury to the patient.

BRIEF SUMMARY OF THE INVENTION

The medical implement of this invention is specifically designed to protect a patient during a seizure. The device is comprised of a flat planar member forming a blade body and adapted to be inserted into a patient's mouth. The blade includes at one end thereof a cushioned pressure pad for depressing and firmly holding the tongue in place to prevent choking or tongue biting. The pressure pad is formed with multiple layers of sterile gauze secured to a tapered nose section of the blade. An alternate construction utilizes cotton swabbing enveloped by a gauze sheath. The cotton is premoistened by partially saturating with an antiseptic solution to prevent adhesion of the pressure pad to the tongue and to further introduce a pleasant taste.

The medical instrument has a mouthpiece forming a bite guard and a depth guide. The mouthpiece is designed for positioning on the blade so that the bite guard will be in registration with the patient's front teeth. The bite guard is fabricated of a soft yieldable material to provide for cushioned impact so as to prevent tooth damage. Furthermore, the thickness of the bite guard is gauged to provide and maintain an air passage essential for the patient's breathing. The mouthpiece also has a flared portion extending outwardly along opposite edges of the blade to form the depth guide. This checks against overinsertion of the instrument and possible injury to the patient's mouth. Further, the instrument cannot fall into the patient's throat when left unattended with the instrument in his mouth. Additionally, each of the flared or wing portions of the depth guide is provided with one or more breathing apertures.

The structure of the medical implement of this invention includes a plurality of striations providing a frictional gripping surface.

The blades are preferably fabricated of a smooth hard wood material or of plastic and can be provided in different lengths such as would be suitable for a child patient or an adult. The nose portion of the blade is tapered as illustrated to prevent the pressure pad from slipping off. Additionally, the mouthpiece can be separately assembled on the blade by placing the nose portion through the slot and by sliding the mouthpiece into snap fitting engagement within the recessed area provided on the blade.

The striated portion of the friction grip is preferably formed with recessed insets as shown and can employ a rubber material for providing the requisite coefficient of friction.

Having thus summarized the invention, it will be seen that an object thereof is to provide a medical implement of the general character described herein.

Specifically, it is an object of the instant invention to provide an improved tongue blade for use in furnishing first aid to a seizure victim.

A further object of this invention is to provide an improved tongue blade having a cushioned pressure pad at one end for contacting and holding the patient's tongue.

An additional object of the present invention is to provide an improved tongue blade having a bite guard and integral depth guide for protecting the patient's teeth and providing a clear air passageway through the mouth.

An additional object of this invention is to provide an improved tongue blade having a friction gripping handle portion to facilitate hand manipulation of the instrument.

The above and other objects, features and advantages of this invention will be apparent from the following description of the preferred embodiment when considered in connection with the accompanying drawings.

BRIEF DESCRIPTION OF THE DRAWINGS

In the accompanying drawings in which is shown the preferred embodiment of this invention.

DETAILED DESCRIPTION OF THE INVENTION

Figure 1:
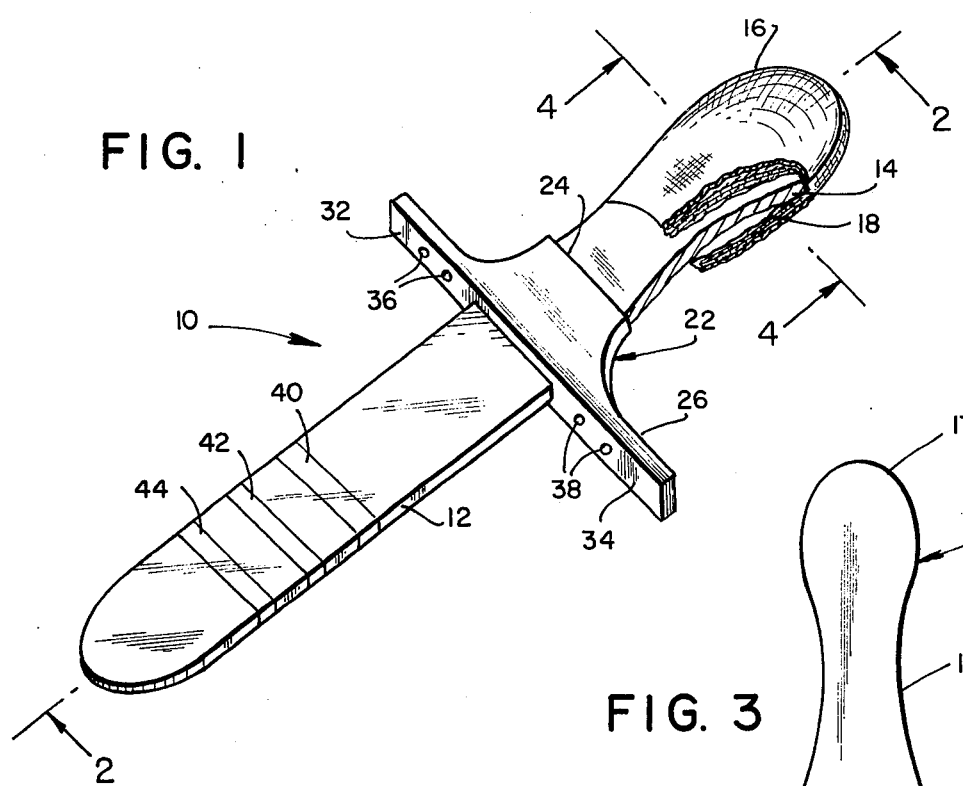
FIG. 1 is a pictorial representation of the improved tongue blade with a portion of the pressure pad being broken away.
Figure 3:
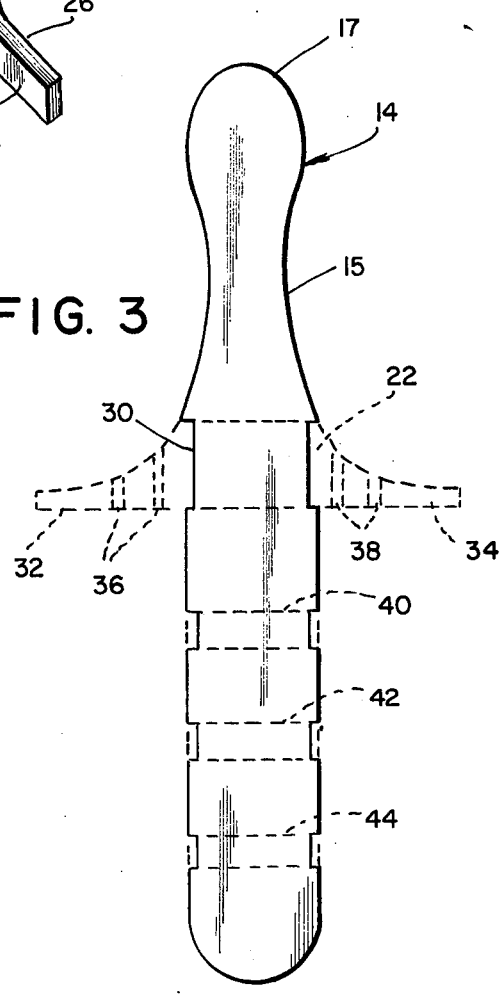
FIG. 3 is a plan view of the blade portion with the bite guard and frictional gripping striations being shown in broken line.

Referring now in detail to the drawings, the reference numeral 10 denotes generally a preferred embodiment of a seizure tongue blade of this invention. The seizure tongue blade 10 is comprised of a planar body portion 12 having a tapered nose section 14 as shown in FIG. 3. The nose section 14 has a necked down portion 15 of reduced width dimension and terminates in a flared rounded head 17. The blade body 12 is preferably fabricated from a smooth hard wood or thermoplastic material. The typical dimensions of the blade body 12 are from 13.7 cm. to 17.5 cm. in length, from 0.3 cm. to 0.9 cm. in thickness and from 1.9 cm. to 2.2 cm. in width at its widest dimension. The particular size and dimensions would be scaled within these ranges for particular applications, such as for children or adults.

The tapered nose section 14 is adapted to support a cushioned pressure pad 16. The pressure pad 16 is formed by the application of several layers of sterile gauze completely surrounding the tapered nose section 14 and anchored in place by a suitable fastening material such as a strip of adhesive 20. The tapered configuration of the nose section 14 will prevent the pressure pad 16 from sliding disengagement in the event a force is exerted tending to pull the pressure pad 16 from the blade body 12.

A feature of this invention includes the incorporation of a mouthpiece 22. The mouthpiece 22 includes a bite guard 24 and a depth guide 26. The mouthpiece 22 is adapted to be assembled on the blade body 12 by inserting the tapered nose section 14 through a slot 23 provided in the mouthpiece 22 for snap-fitting engagement within a recessed area 30 provided in the blade body 12 for accommodating the mouthpiece 22. The bite guard 24 is positioned on the blade body 12 as to be in registration with the confronting upper and lower front teeth of a patient when the seizure tongue blade is inserted within the patient's mouth. Accordingly, the mouthpiece 22 is preferably fabricated of a soft pliable material such as rubber or other such resilient material so as to protect the patient's teeth upon contact and to cushion the impact. The thickness of the bite guard is typically between 0.6 cm. and 1.9 cm. and thus will displace the front teeth and lips to provide an air passageway. Rearwardly positioned from the bite guard 24 is the depth guide 26 having flange extension wings 32, 34 extending transversely with respect to the blade body 12. These wings 32, 34 typically have a combined overall span in the range of 7.5 cm. to 10 cm. and are adapted to contact the mouth periphery to limit overinsertion of the seizure tongue blade 10. A plurality of breathing apertures such as those shown at 36, 38 are provided within the respective wing members 32, 34 and extend therethrough. Progressing further along the blade body 12 are positioned a number of striations 40, 42, 44 which are located in the handle portion of the blade body 12. These bands or striations 40, 42, 44 are set into recesses in the blade body 12 to provide a friction gripping surface and are preferably made of rubber or other material which will permit the implement to be firmly gripped. Alternatively, the blade body 12 can be scored to provide a rougher surface.

Figure 4:
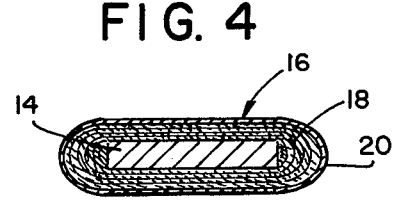
FIG. 4 is a sectional view taken substantially along line 4—4 of FIG. 1 and shows the arrangement of plural layers of gauze being affixed around the blade portion.
Figure 4A:
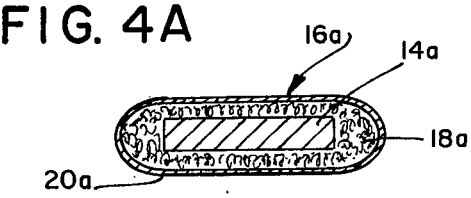
FIG. 4A is a sectional view corresponding to FIG. 4, however showing a modified construction wherein moist cotton swab is placed around the blade portion and enveloped with a gauze sheath.
Figure 2:
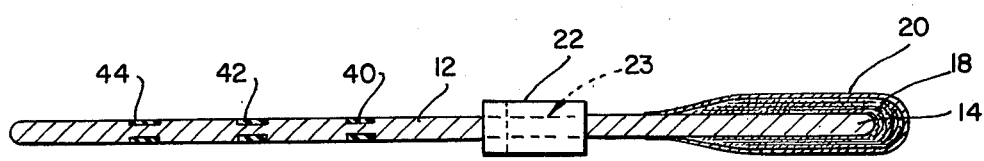
FIG. 2 is a longitudinal sectional view taken substantially along line 2—2 of FIG. 1 and shows the cushioned pressure pad at one end including the arrangement of a bite guard and integral depth guide.

FIG. 4A is illustrative of a modified embodiment of a cushioned pressure pad 16a. In this variant a cotton swab material 18a is placed around the nose portion 14a and held in place by an enveloping gauze sheath 20a. The cotton swab 18a is premoistened with an antiseptic solution and can be flavored to provide a pleasant taste.

The seizure tongue blade 10 should be packaged in a suitable envelope or hermetically sealed in a container to insure that it remains in a sterile condition prior to use. Further, this will prevent evaporation of the solution described in the modified embodiment.

In operation, the seizure tongue blade 10 is adapted to be inserted into the mouth of a seizure victim with the pressure pad 16 being applied to depress the victim's tongue to provide a clear air passage and to prevent biting of the tongue. The mouthpiece 22 provides a protective bite guard 24 which will receive the patient's upper and lower front teeth and maintain an open space between the teeth to permit breathing and release of saliva as when the patient's face is turned to the side. The depth guide 26 is adapted for abutment against the patient's mouth and is used as a precautionary measure to prevent overinsertion of the seizure tongue blade 10 which might result in damage to the surrounding tissue or possible choking. As a further aid to permit proper breathing, the apertures 36, 38 provide an air passage to the patient's mouth. The cushioned pressure pad 16 is adapted to firmly hold the patient's tongue in position.

In the alternate embodiment described, the pressure pad 16a is premoistened and will thus prevent adherence to surrounding tissue. A flavoring substance may be added to the moistening agent to provide a pleasant taste upon removal.

As other possible embodiments of the present invention and various changes might be incorporated by those skilled in the art without departing from the spirit of the invention, it should be understood that the invention is not limited to what is described in the specification and should not be interpreted in a limiting sense.

Having thus described the invention, there is claimed as new and desired to be secured by Letters Patent:

1. A medical implement in the form of a tongue blade suitable for use in rendering first aid assistance to seizure patients comprising a planar blade body having pressure pad means secured at one end thereof for contacting the patient's tongue to hold same firmly in place, mouthpiece means attached to the blade body being located for registration with the confronting upper and lower teeth of the patient for providing protective cushioned tooth impact, said mouthpiece further having depth guide means extending transversely from the blade body for contacting the periphery of the mouth to prevent overinsertion of the tongue blade.

2. A medical implement as claimed in claim 1 wherein the blade body has a tapered nose portion of reduced width dimension and terminates in a flared rounded head, said configuration facilitating the securement of the pressure pad to the blade body.

3. A medical implement as claimed in claim 2 includes plural layers of cushioning material surrounding the nose portion and fastening means for securing same thereto.

4. A medical implement as claimed in claim 2 wherein the pressure pad includes premoistened cotton swab surrounding the nose portion and fastening means for securing same thereto.

5. A medical instrument as claimed in claim 2 wherein the mouthpiece has a slotted passageway therethrough and the blade body has conforming recesses for receiving the mouthpiece to effect a snap fitting assembly.

6. A medical instrument as claimed in claim 5 wherein the mouthpiece is fabricated of a soft pliable material.

7. A medical implement as claimed in claim 1 wherein the mouthpiece includes a bite guard having a height dimension greater than the thickness of the blade body and being adapted to maintain a displacement between the upper and lower front teeth to provide an air passageway through the mouth.

8. A medical implement as claimed in claim 7 wherein the depth guide means includes two wing sections, said wing sections being adapted for abutment against the patient's mouth.

9. A medical implement as claimed in claim 8 wherein said wing sections are provided with a plurality of breathing apertures.

10. A medical implement as claimed in claim 7 further including a finger gripping portion for increasing frictional resistance and providing a firm grasp.

* * * * *